United States Patent
Merkel et al.

(10) Patent No.: US 7,071,368 B1
(45) Date of Patent: Jul. 4, 2006

(54) METHOD OF MAKING 1,1,1-TRIFLUOROETHANE

(75) Inventors: Daniel C. Merkel, West Senaca, NY (US); Hsueh Sung Tung, Getzville, NY (US); Robert C. Johnson, Lancaster, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/054,029

(22) Filed: Feb. 9, 2005

(51) Int. Cl.
 *C07C 17/00* (2006.01)
 *C07C 19/00* (2006.01)
 *C07C 21/00* (2006.01)
 *C07C 23/00* (2006.01)
 *C07C 25/00* (2006.01)

(52) U.S. Cl. ............ 570/101; 570/123; 570/161; 570/163; 570/164; 570/165; 570/166; 570/167; 570/168

(58) Field of Classification Search ............ 570/101, 570/123, 161, 163, 164, 165, 166, 167, 168
See application file for complete search history.

(56) References Cited

U.S. PATENT DOCUMENTS

| 2,478,932 | A | 8/1949 | Miller et al. .............. 260/653 |
|---|---|---|---|
| 4,766,258 | A | 8/1988 | Komatsu et al. ............ 570/168 |
| 4,968,850 | A | 11/1990 | Franklin et al. ............ 570/166 |
| 5,574,191 | A | 11/1996 | Balthasart et al. .......... 570/166 |
| 5,770,779 | A | 6/1998 | Nappa et al. ............... 570/168 |
| 6,080,899 | A | 6/2000 | Bradley et al. ............. 570/167 |
| 6,339,178 | B1 * | 1/2002 | Lantz et al. ................ 570/167 |
| 6,630,610 | B1 | 10/2003 | Swaim et al. ............... 570/167 |

FOREIGN PATENT DOCUMENTS

| CN | 1106779 | 2/1995 |
|---|---|---|
| EP | 0 712 826 A1 * | 8/1995 |
| JP | 8217704 | 8/1996 |
| KR | 184381 | 5/1999 |
| KR | 2000027318 | 5/2000 |
| RU | 2160245 C2 | 5/1998 |
| WO | WO 96/05156 | 2/1996 |

* cited by examiner

*Primary Examiner*—Johann Richter
*Assistant Examiner*—Chukwuma Nwaonicha
(74) *Attorney, Agent, or Firm*—Colleen D. Szuch

(57) ABSTRACT

A process for producing 1,1,1-trifluoroethane (HFC-143a) which process comprises reacting hydrogen fluoride with vinylidene chloride along with one or more of 1,1,-dichloro-1-fluoroethane (HCFC-141b), 1-chloro-1,1-difluoroethane (HCFC-142b) and 1,1,1-trichloroethane (HCC-140a) in the presence of pentavalent antimony as a fluorination catalyst under conditions to produce 1,1,1-trifluoroethane (HFC-143a), generally in yields of 90% or more.

11 Claims, No Drawings

METHOD OF MAKING 1,1,1-TRIFLUOROETHANE

FIELD OF THE INVENTION

This invention relates to a method of producing 1,1,1-trifluoroethane (HFC-143a). Instead of the conventional commercial method of using pure component, such as 1,1,1-trichloroethane (HCC-140a) as the feedstock to a liquid-phase reactor system, this invention relates to the use of alternative organic feed stocks comprising 1,1-dichloro-ethene (vinylidene chloride) in combination with one or more of 1,1-dichloro-1-fluoroethane (HCFC-141 b), and 1-chloro-1,1-difluoroethane(HCFC-142b) and 1,1,1-trichloroethane (HCC-140a) to make HFC-143a.

BACKGROUND TO THE INVENTION

Mechanical refrigeration systems, and related heat transfer devices such as heat pumps and air conditioners, using refrigerant liquids are well known in the art for industrial, commercial and domestic uses. Chlorofluorocarbons (CFCs) were developed in the 1930s as refrigerants for such systems. However, since the 1980s the effect of CFCs on the stratospheric ozone layer has become the focus of much attention. In 1987 a number of government signed the Montreal Protocol to protect the global environment setting forth a timetable for phasing out the CFC products. Subsequent amendments to this protocol accelerated the phase-out of these CFCs and also scheduled the phase-out of HCFCs. Thus, there is a requirement for a non-flammable, non-toxic alternative to replace these CFCs and HCFCs. In response to such demand industry has developed a number of hydrofluorocarbons (HFCs), which have a zero ozone depletion potential.

Hydrofluorcarbons such as difluoromethane (HFC-32), 1,1,1-trifluoroethane (HFC-143a) and 1,1-difluoroethane (HFC-152a) have essentially no ozone depletion potential (ODP) and therefore, they have been found to be acceptable refrigerants and, in some cases, as potential blowing agents in the production of plastic foams.

1,1,1-Trifluoroethane (HFC-143a) is a component of the commercially available non-ozone depleting refrigerant blend 507A (a.k.a. AZ-50). One of the commercial processes for making HFC-143a is by reacting 1,1,1-trichloroethane (HCC-140a) with HF directly. HCC-140a was once one of the most highly produced chemicals in the world. It was once used as a solvent and more recently as a raw material for making 1,1-dichloro-1-fluoroethane (HCFC-141b). With the phase out of CFC's and HCFC's as stipulated by the Montreal Protocol, the production of HCC-140a has decreased dramatically. By the "rules" of supply and demand the price has increased dramatically. Similarly, most uses of HCFC-141b are being legislated away; the economic impact of this can result in relatively high cost for this as a feedstock, since other uses are prohibited. Thus, there is a need for an alternate method for the manufacture of HFC-143a that can use, in part or all, alternate organic starting materials and combinations there of.

U.S. Pat. No. 2,478,932, Miller et al., Allied Chemical & Dye relates to gas-phase reactions for the fluorination of 1,1,1-dichlorofluoroethane using an aluminum fluoride or complex basic aluminum fluoride catalyst. Such gas phase reaction are not really desirable because they must operate at higher temperatures, generally create more byproducts, have lower volumetric throughput, and have short catalyst life.

U.S. Pat. No. 4,766,258, Komatsu et al., Asahi Kasei, relates to liquid phase production of HFC-143a from individual hydrochlorocarbons using a tin-based catalyst.

U.S. Pat. No. 4,968,850, Franklin et al., Solvay & Cie, relates to liquid phase production of HFC-143a from unsaturated chlorocarbons, such as vinylidene chloride, using tin-based catalyst and an organophosphorus inhibitor. The amount of HFC-143a produced is very little, i.e., 2% or less.

U.S. Pat. No. 5,574,191, Balthasart et al., Solvay & Cie, relates to co-production of HFC-143a with vinylidene fluoride and at least one of 1-chloro-1,1-difluoroethane (HCFC-142b) and 1,1-dichloro-1-fluoroethane (HCFC-141b) in liquid phase without use of a catalyst. The process example in this patent produced only 6.1% HFC-143a.

U.S. Pat. No. 5,770,779, Nappa, et al., E.I. duPont de Nemours and Company, relates to production of HFC-143a using tin-based catalyst and at least one compound selected from metal and nonmetal alkoxides U.S. Pat. No. 6,080,899, Bradley, et al., AlliedSignal Inc., relates to operating conditions for producing compounds such as HFC-143a including a solvent not taking part in the reaction.

U.S. Pat. No. 6,339,178, Lantz, et al., Atofina, relates to production of HFC-143a from HFCF-142b alone in the presence of a fluorination catalyst.

U.S. Pat. No. 6,630,610, Swain, et al., AlliedSignal Inc., relates to operating conditions for producing HFC-143a from 1,1,1-trichloroethane (HCC-140a).

WO 96/05156, Swain, AlliedSignal Inc., relates to production of HFC-143a from HCC-140a alone in the absence of a solvent.

JP 8-217704 relates to co-production of HFC-143a with HFC-32, using HCC-140a as the feed for the HFC-143a.

Korean Patent 2000027318, Na, et al., describes preparing HFC-143a in liquid phase using antimony catalyst from a mixture of HCFC-141b and HCFC-142b.

Korean Patent 184381 describes co-production of HFC-143a and HCFC-142b in the liquid phase without catalyst.

Russian Patent 2 160 245, Orlov, et al., describes co-production of HFC-143a, HCFC-142b, and HCFC-141b from HCC-140a or vinylidene chloride in liquid phase.

Chinese Patents 1106779 and 1044802 relate to production of HFC-143a from 1-chloro-1,1-difluoroethane (HCFC-142b) in liquid phase using antimony-based catalyst.

In view of the rapidly rising cost of 1,1,1-trichloroethane there is a need for an alternative process that enables one to produce HFC-143a with different reactant(s), which can change depending upon fluctuations in the prices of these reactant raw materials.

SUMMARY OF THE INVENTION

According to the invention there is provided a process for producing 1,1,1-trifluoroethane (HFC-143a) which comprises reacting vinylidene chloride and one or more of 1,1,-dichloro-1-fluoroethane (HCFC-141b), 1-chloro-1,1-difluoroethane (HCFC-142b) and 1,1,1-trichloroethane (HCC-140a) with hydrogen fluoride in the presence of pentavalent antimony compound as a fluorination catalyst under conditions to produce 1,1,1-trifluoroethane (HFC-143a). In accordance with the method of this invention, when one employs vinylidene chloride as one of the feedstock reactants along with one or more of the other halogenated reactants, one can unexpectedly produce 1,1,1-trifluoroethane (HFC-143a) in yields of 90% or more, even 95% or more, of the total weight of halogenated hydrocarbons produced. Moreover, with the method of this invention, the flexibility in selecting the combinations of starting reactant feeds enables one to readily change the feedstocks depending upon the fluctuation in price of the raw material for the feedstocks.

DETAILED DESCRIPTION OF THE INVENTION

There is provided, in accordance with this invention, a process for producing 1,1,1-trifluoroethane (HFC-143a) which process comprises reacting hydrogen fluoride with vinylidene chloride in combination with one or more of 1,1,-dichloro-1-fluoroethane (HCFC-141b), 1-chloro-1,1-difluoroethane (HCFC-142b) and 1,1,1-trichloroethane (HCC-140a) in the presence of pentavalent antimony as a fluorination catalyst under conditions to produce 1,1,1-trifluoroethane (HFC-143a).

In accordance with the process of this invention, vinylidene chloride along with any combination of one or more of 1,1,-dichloro-1-fluoroethane (HCFC-141b), 1-chloro-1,1-difluoroethane (HCFC-142b) and 1,1,1-trichloroethane (HCC-140a) is reacted with hydrogen fluoride to produce high levels of 1,1,1-trifluoroethane (HFC-143a). Preferably, the weight ratio of amount of vinylidene chloride employed in the reaction to the amount of the one or more of 1,1-dichloro-1-fluoroethane (HCFC-141 b), 1-chloro-1,1-difluoroethane (HCFC-142b) and 1,1,1-trichloroethane (HCC-140a) will be from about 90/10 to about 10/90, more preferably from about 50/50 to about 25/75.

The reaction is conducted as a liquid phase reaction and may be conducted in a batch, semi-continuous or fully continuous manner. A fully continuous reaction is preferred. Any suitable reactor may be employed such as Hastelloy, Inconel, Monel, stainless steel, steel, or in a Teflon lined reaction vessels, with or without agitation.

The reaction is preferably conducted in the presence of a suitable pentavalent antimony fluorination catalyst. Such pentavalent antimony compounds may be antimony halides, mixed pentavalent antimony halides, or a mixture of pentavalent antimony halides. More preferably the catalyst is antimony pentachloride ($SbCl_5$) or antimony pentafluoride ($SbF_5$), most preferably antimony pentachloride.

The amount of fluorination catalyst employed in the process of this invention may be any suitable amount. Generally, the amount of catalyst employed will be an amount such that the weight ratio of catalyst to HF reactant is from about 5:95 to about 99.9:0.1, preferably from about 20:80 to about 99.9:01, even more preferably from about 30:70 to about 99.9:0.1, and most preferably about 84:16.

Since the presence of water will tend to deactivate the catalyst, the hydrogen fluoride reactant is preferably substantially anhydrous. By "substantially anhydrous" is meant that the hydrogen fluoride contains less than about 0.05% water, preferably less than about 0.02% water. It will be appreciated that the presence of water can be compensated for, at least in part, by the use of increased levels of catalyst in the reaction. The amount of hydrogen fluoride reactant employed in the reaction of this invention may be any suitable amount. Preferably, the mole ratio of hydrogen fluoride reactant to the total of the organic halide reactants will be in the range of from about 1/1 to about 25/1; more preferably from about 1/1 to about 20/1; and most preferably from about 1.5/1 to about 15/1.

Any suitable temperature or pressure may be employed in the reaction of this invention. The temperature employed will preferably be from about 0° C. to about 200° C., more preferably from about 20° C. to about 150° C., and most preferably from about 40° C. to about 120° C. The pressure employed will be determined by whether the reaction is run in continuous or batch mode and will preferably be from about 0 to about 700 psig (about 0 to about 49.215 $kg/cm^2$), more preferably from about 5 to about 300 psig (about 0.352 to about 21.097 $kg/cm^2$), and most preferably from about 15 to about 150 psig (about 1.055 to about 10.546 $kg/cm^2$) in continuous mode. Higher pressures may be employed in batch mode. The reaction may be conducted in a continuous mode or in a batch mode using any suitable time period, preferably over a period of from about 1 second to about 2 hours, more preferably over a period of from about 5 seconds to about 60 minutes.

In a further embodiment of the method of this invention, chlorine, most preferably in the form of chlorine liquid or gas, may be introduced into the reaction mixture in the reaction vessel to keep the catalyst in its pentavalent state, i.e., its active state.

The invention is illustrated by, but not limited to, the following synthesis examples.

EXAMPLE 1

A one-gallon Parr autoclave with internal stirring was used. Antimony pentachloride was added to the autoclave. An equimolar amount of HF was added to partially fluorinate the antimony (the autoclave was not vented), and the agitated reactor was heated to 90° C. Then a mixture of 75/25 (wt %) of vinylidene chloride to HCFC-141b, plus 2.5 moles of HF per mole of organic was added to the autoclave. The autoclave was maintained at 90° C. for thirty minutes. The pressure rose to 530 psig (37.263 $kg/cm^2$) during this time. Then the reactor was vented to cold traps, and the reaction product washed and analyzed. The weight % of $SbCl_5$ to HF was in about an 84/16 ratio. The result was a 91.33% conversion to 1,1,1-trifluoroethane (HFC-143a), with 8.55% byproducts (defined as compounds other than HFC-143a, HCFC-142b, HCFC-141b, HCC-140a, or vinylidene chloride).

EXAMPLE 2

The reaction was the same as in Example 1, but the pressure rise reached 600 psig (42.484 $kg/cm^2$). The result was a 91.90% conversion to 1,1,1-trifluoroethane (HFC-143a), with 8.06% byproducts.

EXAMPLE 3

The reaction was the same as in Example 1, but a 50/50 wt % mixture of vinylidene chloride to HCFC-141b was employed as the organic feed, and a 2.75:1 mole ratio of HF to organic was employed. The weight % of $SbCl_5$ to HF was in about an 84/16 ratio. The pressure reached 540 psig (37.966 $kg/cm^2$) and all reactants were held in the batch reactor for 30 min. The result was a 71.43% conversion to 1,1,1-trifluoroethane (HFC-143a), with 8.41% byproducts.

EXAMPLE 4

This reaction was run at the same conditions as Example 3. The result was a 95.26% conversion to 1,1,1-trifluoroethane (HFC-143a), with 4.70% byproducts.

EXAMPLE 5

This reaction was run at the same conditions as Examples 3 and 4. The result was a 94.93% conversion to 1,1,1-trifluoroethane (HFC-143a), with 5.02% byproducts.

EXAMPLE 6

The reaction was conducted in the same manner as in Example #1, except used a 75/25 wt % mixture of vinylidene chloride to HCFC-141b as the organic feed and a 3.0:1 mole ratio of HF to organic was quickly added to the reactor with agitation. The weight % of $SbCl_5$ to HF was in about an 84/16 ratio. The pressure was about 490 psig (34.450 kg/cm$^2$) and all reactants were held in the batch reactor for 30 min. The result was a 91.59% conversion to 1,1,1-trifluoroethane (HFC-143a), with 8.33% byproducts.

EXAMPLE 7

The conditions of this reaction were the same as in Example 6. The result was a 91.97% conversion to 1,1,1-trifluoroethane (HFC-143a), with 7.98% byproducts.

EXAMPLE 8

The reaction conditions were the same as in Example 1, except a 50/50 wt % mixture of vinylidene chloride to HCC-140a was used as the organic feed and a 3.2:1 mole ratio of HF to organic was quickly added to the reactor with agitation. The weight % of $SbCl_5$ to HF was in about an 84/16 ratio. The pressure was about 530 psig (37.623 kg/cm$^2$) and all reactants were held in the batch reactor for 30 min. The result was a 96.63% conversion to 1,1,1-trifluoroethane (HFC-143a), with 3.28% byproducts.

EXAMPLE 9

The reactions conditions were the same as in Example 8. The result was a 96.41% conversion to 1,1,1-trifluoroethane (HFC-143a), with 3.55% byproducts.

EXAMPLE 10

The reaction was conducted under the same conditions as in Example 1, except a 50/50 wt % mixture of vinylidene chloride to HCFC-142b as the organic feed was used, and a 2.6:1 mole ratio of HF to organic was quickly added to the reactor with agitation. The weight % of $SbCl_5$ to HF was in about an 84/16 ratio. The pressure was about 525 psig (36.911 kg/cm$^2$) and all reactants were held in the batch reactor for 30 min. The result was a 94.50% conversion to 1,1,1-trifluoroethane (HFC-143a), with 5.45% byproducts.

EXAMPLE 11

The reaction conditions were the same as in Example 10. The result was a 96.81% conversion to 1,1,1-trifluoroethane (HFC-143a), with 3.13% byproducts.

EXAMPLE 12

The reaction conditions were the same as in Example 1, but a 25/75 wt % mixture of vinylidene chloride to HCFC-141b as the organic feed was used and a 2.48:1 mole ratio of HF to organic was quickly added to the reactor with agitation. The weight % of $SbCl_5$ to HF was in about an 84/16 ratio. The pressure was about 525 psig (36.911 kg/cm$^2$) and all reactants were held in the batch reactor for 30 min. The result was a 98.62% conversion to 1,1,1-trifluoroethane (HFC-143a), with 1.35% byproducts.

EXAMPLE 13

The reaction conditions were the same as in Example 12. The result was a 98.15% conversion to 1,1,1-trifluoroethane (HFC-143a), with 1.81% byproducts.

EXAMPLE 14

The reaction conditions were the same as in Example 1, but used a 25/75 wt % mixture of vinylidene chloride to HCC-140a as the organic feed and a 2.51:1 mole ratio of HF to organic was quickly added to the reactor with agitation. The weight % of $SbCl_5$ to HF was in about an 84/16 ratio. The pressure was about 550 psig (38.669 kg/cm$^2$) and all reactants were held in the batch reactor for 30 min. The result was a 95.40% conversion to 1,1,1-trifluoroethane (HFC-143a), with 4.52% byproducts.

EXAMPLE 15

The reaction conditions were the same as in Example 14. The result was a 95.81% conversion to 1,1,1-trifluoroethane (HFC-143a), with 4.12% byproducts.

EXAMPLE 16

This reaction was run using a 25/75 wt % mixture of vinylidene chloride to HCFC-142b as the organic feed and a 2.3:1 mole ratio of HF to organic was quickly added to the reactor with agitation, similar to the conditions were as in Example 1. The weight % of $SbCl_5$ to HF was in about an 84/16 ratio. The pressure was about 580 psig (40.778 kg/cm$^2$) and all reactants were held in the batch reactor for 30 min. The result was a 99.08% conversion to 1,1,1-trifluoroethane (HFC-143a), with 0.92% byproducts.

From these examples, it can be seen that mixtures of several of these feed combinations in a wide range of proportions can result in high yields of the desired 1,1,1-trifluoroethane (HFC-143a) product, and with a favorable impact on the formation of undesirable byproducts.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

What is claimed is:

1. A process for producing 1,1,1-trifluoroethane (HFC-143a) which comprises reacting vinylidene chloride and at least one of 1,1,-dichloro-1-fluoroethane (HCFC-141b), 1-chloro-1,1-difluoroethane (HCFC-142b) and 1,1,1-trichloroethane (HCC-140a) with hydrogen fluoride in the presence of pentavalent antimony as a fluorination catalyst under conditions to produce 1,1,1-trifluoroethane (HFC-143a).

2. A process according to claim 1 wherein the hydrogen fluoride is reacted with a combination of vinylidene chloride and 1,1,-dichloro-1-fluoroethane (HCFC-141b).

3. A process according to claim 1 wherein the hydrogen fluoride is reacted with a combination of vinylidene chloride and 1-chloro-1,1-difluoroethane (HCFC-142b).

4. A process according to claim 1 wherein the hydrogen fluoride is reacted with a combination of vinylidene chloride and 1,1,1-trichloroethane (HCC-140a).

5. A process according to claim 1 wherein the pentavalent antimony fluorination catalyst is selected from the group consisting of pentavalent antimony halides, mixed pentavalent antimony halides and mixtures of pentavalent antimony halides.

6. A process according to claim 5 wherein the pentavalent antimony catalyst is antimony pentachloride.

7. A process according to claim 1 wherein the weight ratio of vinylidene chloride reactant to the one or more of 1,1,-dichloro-1-fluoroethane (HCFC-141 b), 1-chloro-1,1-difluoroethane (HCFC-142b) and 1,1,1-trichloroethane (HCC-140a) reactants is from about 90:10 to about 10:90.

8. A process according to claim 1 wherein the amount of 1,1,1-trifluoroethane (HFC-143a) produced is at least 90% of the halogenated hydrocarbons produced.

9. A process according to claim 1 wherein the amount of 1,1,1-trifluoroethane (HFC-143a) produced is at least 95% of the halogenated hydrocarbons produced.

10. A process according to claim 1 wherein the reaction is conducted in the presence of chlorine liquid or gas to maintain the activity of the catalyst.

11. A process according to claim 1 wherein weight ratio of vinylidene chloride reactant to the one or more of 1,1-dichloro-1-fluoroethane (HCFC-141 b), 1-chloro-1,1-difluoroethane (HCFC-142b) and 1,1,1-trichloroethane (HCC-140a) is from about 90:10 to about 10:90, the hydrogen fluoride reactant is substantially anhydrous hydrogen fluoride, the catalyst is antimony pentachloride, the reaction is conducted in the liquid phase at a temperature of from about 40° C. to about 120° C., the reaction is conducted at a pressure of from about 15 to about 150 psig (about 1.055 to about 10.546 kg/cm$^2$), the mole ratio of hydrogen fluoride reactant to organic halide reactants is from about 1/1 to about 20/1, and the amount of 1,1,1-trifluoroethane (HFC-143a) produced is at least 90% of the halogenated hydrocarbons produced.

\* \* \* \* \*